United States Patent
Wiggins (10) Patent No.: US 7,668,738 B2
(45) Date of Patent: Feb. 23, 2010

(54) INSURANCE CLAIM FILING SYSTEM AND METHOD

(75) Inventor: Stephen K Wiggins, Columbia, SC (US)

(73) Assignee: Blue Cross and Blue Shield of South Carolina, Columbia, SC (US)

(*) Notice: Subject to any disclaimer, the term of this patent is extended or adjusted under 35 U.S.C. 154(b) by 1988 days.

(21) Appl. No.: 09/794,741

(22) Filed: Feb. 27, 2001

(65) Prior Publication Data
US 2002/0120473 A1 Aug. 29, 2002

Related U.S. Application Data

(60) Provisional application No. 60/208,553, filed on Jun. 1, 2000.

(51) Int. Cl.
*A61B 5/00* (2006.01)
(52) U.S. Cl. ............ 705/4; 705/2; 705/3; 705/40; 709/224; 709/227; 713/201
(58) Field of Classification Search ............ 705/4, 705/3, 2, 40; 709/224, 227; 713/201
See application file for complete search history.

(56) References Cited

U.S. PATENT DOCUMENTS

| | | | | |
|---|---|---|---|---|
| 4,858,121 A * | 8/1989 | Barber et al. | ............ | 705/2 |
| 5,070,452 A | 12/1991 | Doyle, Jr. et al. | ............ | 705/2 |
| 5,235,507 A | 8/1993 | Sackler et al. | ............ | 705/2 |
| 5,235,702 A | 8/1993 | Miller | ............ | 707/102 |
| 5,359,509 A | 10/1994 | Little et al. | ............ | 705/2 |
| 5,644,778 A | 7/1997 | Burks et al. | ............ | 705/2 |
| 5,848,396 A | 12/1998 | Gerace | ............ | 705/10 |
| 5,909,581 A * | 6/1999 | Park | ............ | 717/170 |
| 5,930,759 A * | 7/1999 | Moore et al. | ............ | 705/2 |
| 5,950,169 A * | 9/1999 | Borghesi et al. | ............ | 705/4 |
| 5,999,741 A * | 12/1999 | May et al. | ............ | 717/173 |
| 6,047,268 A * | 4/2000 | Bartoli et al. | ............ | 705/35 |
| 6,199,077 B1 * | 3/2001 | Inala et al. | ............ | 715/501.1 |

(Continued)

OTHER PUBLICATIONS

Netscape Cookie Specification: http://wp.netscape.com/newsref/std/cookie_spec.html.*

(Continued)

*Primary Examiner*—James A Kramer
*Assistant Examiner*—Martin A Gottschalk
(74) *Attorney, Agent, or Firm*—Michael A. Mann; Nexsen Pruet, LLC (57) ABSTRACT

A method and system for enabling a service provider to file insurance claims electronically directly with the payer rather than through a clearinghouse. The system has two components interacting with an existing practice management system of a service provider and with online claim filing systems of insurance payers. The first is a software application installed on the service provider's computer to seek out billing information and create files suitable for filing of formatted claims with the payer's web sites. The second component is a web portal that interacts with both the first component and the payers' web sites to keep the former with formatting requirements and to facilitate filing of the claims electronically. The system uses a software "cookie" to convey instructions to the first component so that it can automatically connect to the appropriate page of each payer's web site.

12 Claims, 3 Drawing Sheets

U.S. PATENT DOCUMENTS 6,341,265 B1 * 1/2002 Provost et al. .................. 705/4
6,343,271 B1 * 1/2002 Peterson et al. ................. 705/4
6,484,178 B1 * 11/2002 Bence et al. ................. 707/101
6,603,464 B1 * 8/2003 Rabin ......................... 345/179
6,915,266 B1 * 7/2005 Saeed et al. .................... 705/2
2001/0041993 A1 * 11/2001 Campbell ...................... 705/4

OTHER PUBLICATIONS

Goedert, Joseph. "Managed Care Changes the Clearinghouse Market." Health Data Management, May 1996, p. 75.*

* cited by examiner

INSURANCE CLAIM FILING SYSTEM AND METHOD

PRIORITY CLAIM

The applicant claims the benefit of the filing date of U.S. provisional patent application Ser. No. 60/208,553, filed Jun. 1, 2000.

FIELD OF THE INVENTION

The present invention relates generally to the processing of insurance claims. In particular, the present method and system relates to filing claims electronically.

BACKGROUND OF THE INVENTION

The medical services industry is huge—measured in trillions of dollars of goods and services each year—but is highly fragmented. The overwhelming majority of goods and services are rendered by doctors' offices, clinics, pharmacies, and individual hospitals scattered throughout the United States.

Because a large percentage of the expenditures on medical goods and services are not anticipated, most people prefer to rely on insurance to bear at least a part of the cost. Health insurance has in fact come to be considered an important type of insurance to have and employers generally find health insurance for their employees and their employees' families to be an important benefit of employment. Although some employers decide to fund the insurance coverage themselves—and are referred to as "self-insured"—most businesses contract with third parties to provide medical insurance to their employees.

For those who are not employed or not part of a family of an insured employee, such as those who are retired and the indigent, government programs such as Medicare and Medicaid sometimes provide the equivalent of private insurance. Thus, the majority of the public is covered by private insurance or an equivalent government program.

From the large number of people who are covered by health insurance, through all of the many organizations who provide health care to them, comes a river of insurance claims to be processed. Currently, approximately nine medical insurance claims are processed per person per year in the United States. Both the insured and those rendering health care depend on the efficient processing of these claims for payment for those services. In many cases the insured individuals will assign their right to collect payment from the insurance carrier to the service providers.

Because of their substantial and widespread dependence on revenues from insurance companies, the service providers have taken over the task of filing the claims on behalf of their insured patients to make certain that the claim is properly made and timely payment is received. Naturally, there is widespread use of computers and software to assist in this task.

The process of obtaining reimbursements from a health insurance company for services rendered to patients must be both effective and administratively easy to implement because of the number of claims that need to be made and the large proportion of their revenue dollars that comes back to service providers from health insurance companies. However, electronic claim filing is complicated by the fact that each payer has its own requirements for a proper claim.

Typically, in the past, heavy use has been made of the mail system and facsimile machines to file paper claims. Since the early 1970's, however, proprietary software systems have been developed by individual payers that tie into the software systems operated by the service provider (generally referred to as "practice management systems") to facilitate electronic filing of claims. Practice management systems are in some cases capable of generating the electronic equivalent of the standard Health Care Financing Administration (HCFA) 1500 claim form and transmitting it electronically via a modem and telephone network. However, using systems that are capable of filing claims with only single payers is a piecemeal approach to the overall problem of filing claims in health care practice management where the patients are insured by a number of payers.

A different approach in claim filing has come into widespread use by service providers. This approach relies on intermediate parties, known as clearinghouses, which receive billing files from service providers, sort them by payer, edit them to create claims in the appropriate format for each payer, and request payment from payers on behalf of the service providers. Some clearinghouses receive the billing files as print images from service providers and convert them to an electronic format for further processing and transmission to the payers. Accordingly, Clearinghouses relieve service providers of the burden of meeting the formatting requirements of multiple payers; however, their service comes with an associated cost and introduces a delay in receipt of payment.

Relatively recently, payers have enabled service providers to connect to the payer's web site via the internet for transmission of claims. However, this approach is not practical when a large number of claims is involved.

Thus, there remains a need for a better way for service providers to file claims as automatically as possible with several payers.

SUMMARY OF THE INVENTION

Briefly recited, the present invention is a method and system for enabling a service provider to file insurance claims via the internet directly with the payer rather than through a clearinghouse. The system has three major components. These three components interact with both the practice management system used by the service provider to keep track of patient information including billing information and with the online claim processing systems of participating insurance companies.

The first component is a software application that is installed on the service provider's local computer system. This "resident" software seeks out billing information stored by the practice management system and creates data files suitable for the filing of properly formatted claims with the payers via their web sites. The second component is a web portal that interacts with both the resident software and the payers' web sites to keep the former up to date with the current formatting requirements of the various payers and to facilitate the filing of the claims electronically via the payers' web site. The present system uses a software "cookie" to convey instructions from the payers' web site to the resident software so that the latter can automatically connect to the appropriate pages of each payer's web site automatically for electronic filing the claims. The third component enables the resident software to communicate via an internet connection to non-internet payers.

The filing of claims directly from the service provider rather than through a clearinghouse is an important feature of the present invention. This feature streamlines the process of filing claims so that payment is received sooner. This approach also eliminates the cost and delays introduced by the clearinghouses.

Another major feature of the present invention is the use of a web portal to collect claim format changes from payers' web sites and to convey those format changes to the resident software at the location of individual service providers automatically. This feature enables the software at each service provider to format billing data properly whenever the claims need to be filed.

Another important feature of the present invention is the way in which the local software is instructed where to file claims within multiple payers at each payer's web site. The local software is enabled by use of software "cookies". Cookies are pieces of text that a web server stores on a user's hard disk for subsequent retrieval. Here the cookies are set by the second component of the system, namely, the web portal, for retrieval by the first component, the resident software. When they are retrieved, they are used by the resident software as a website bookmark to enable it to go automatically and directly to the appropriate part of a payer's web site for filing claims.

Another major feature of the present invention is the ability to communicate with insurance companies that do not have a web sight. The resident software initiates a secure communication link with the web portal, which redirects the connection to an access server, and connects to a insurance company's claims collection system.

Other features and their advantages will become apparent to those skilled in the art of processing insurance claims from a careful reading of the Detailed Description of Preferred Embodiments, accompanied by the drawings.

DETAILED DESCRIPTION OF PREFERRED EMBODIMENTS

Figure 1:
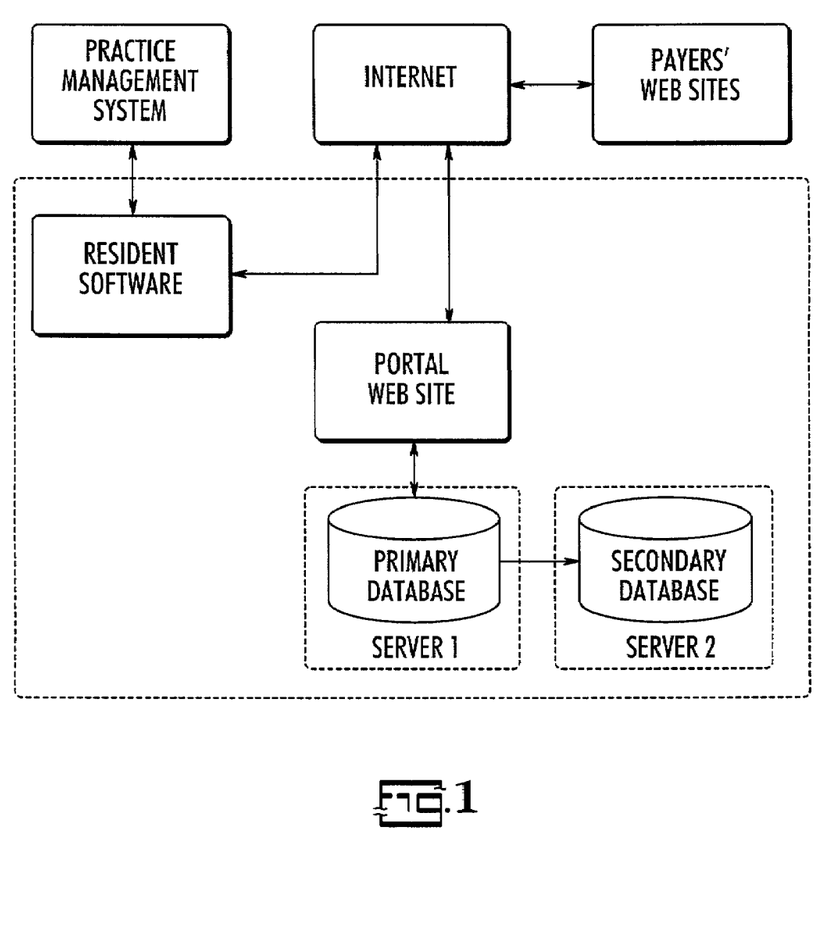
FIG. 1 is a schematic view of the components of the present insurance claim filing system in relation to the practice management system of the service provider and the payers' web sites, according to a preferred embodiment of the present invention.
Figure 2:
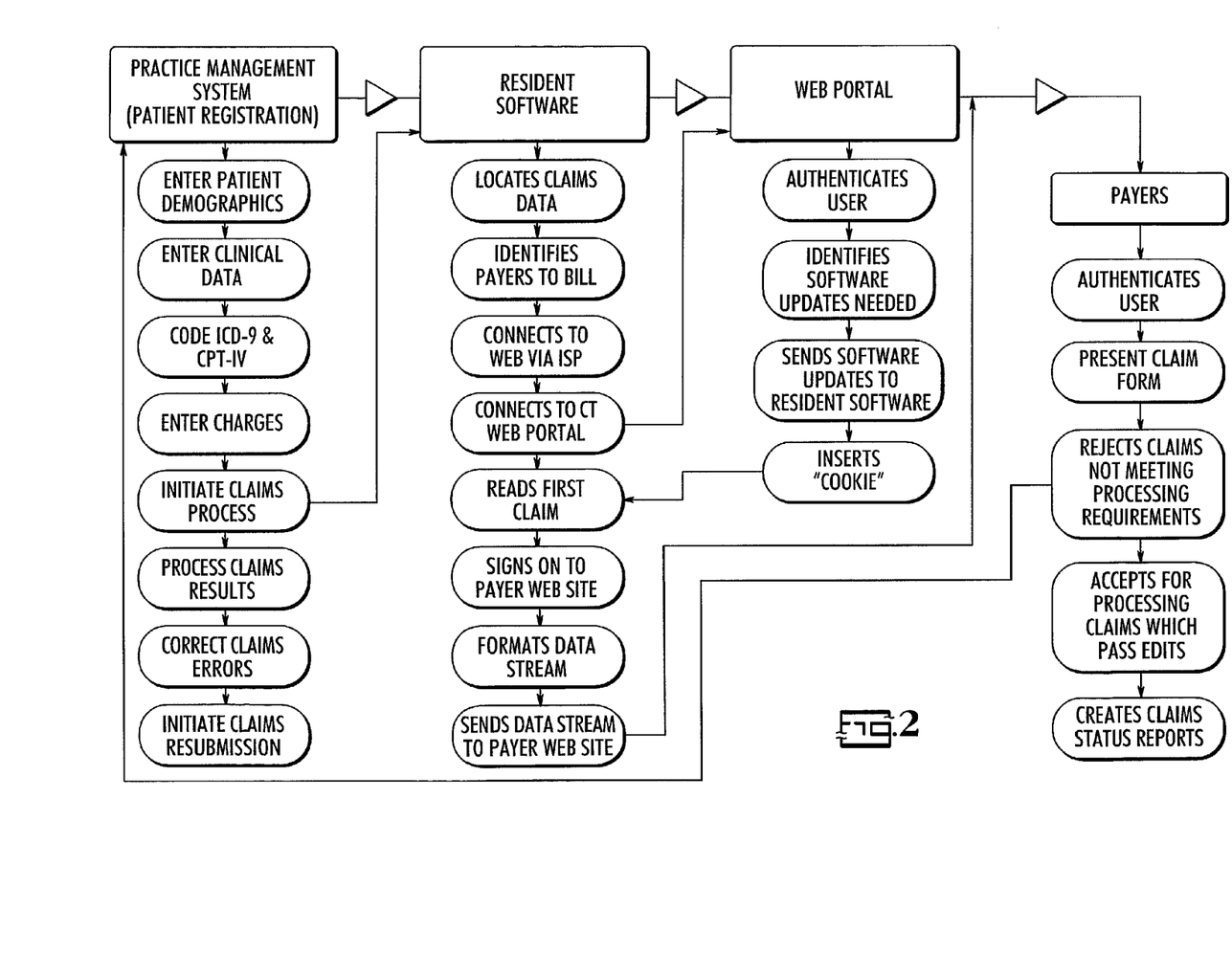
FIGS. 2 and 3 are two parts of a flow chart and schematic diagram of a method and system for obtaining verification of insurance, according to a preferred embodiment of the present method.
Figure 3:
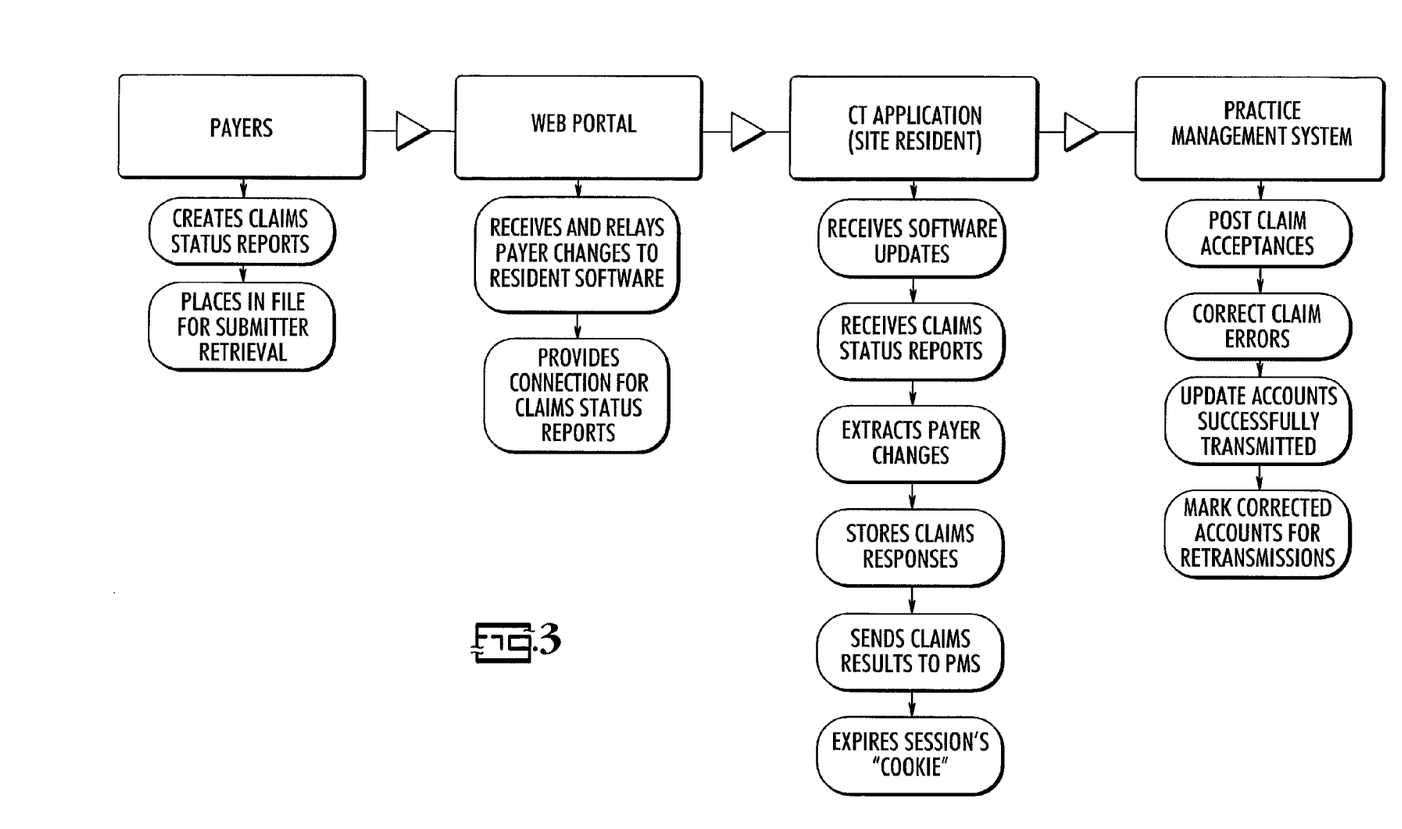

The present invention is a system and method that allow a service provider to file insurance claims automatically and directly over the internet with multiple payers in the current format each payer requires. The invention will be described in the context of a health care service provider and health care insurance but it will be apparent to those skilled in processes for filing formatted requests electronically that the present invention may be applied in these other contexts equally as well.

The term "service provider" is used herein to designate an entity that provides healthcare treatment to the public, such as a doctor's office, a hospital, or a clinic. The term "payer" refers to those organizations that are obliged by statute or contract to pay claims made by customers of service providers for the services they render. Payers include both private insurance companies, self-insured companies, and government and state agencies.

The term "payer" in addition to including insurance companies, self-insured companies and governmental insurance programs, also includes clearinghouses that broker claims for these direct payers.

The term "practice management system" will be used to refer to hardware and the software installed on that hardware that the service provider uses to keep track of patient information and demographics, appointments, billing, clinical data, charges for services rendered and any other relevant matters in order to perform the functions it routinely performs. The service provider will enter various numeric, alpha-numeric, and text information, including coded information such as the diagnosis and treatment, usually using standard codes such as International Classification of Diseases (ICD) code and Current Procedure and Terminology (CPT) code. The service provider enters information into its computers by keystrokes, voice recognition software, scanning or downloading from another source. This information, or at least part of it, is used to generate billing data files for use in preparing a claim. These files may take several forms including images of the HCFA 1500 form and data streams with claims information arranged in fields of various lengths. Although the present invention interfaces with the practice management system to retrieve information, the practice management system is not part of the present invention.

Referring now to the figures, the service provider, in order to avail itself of the present system, must have software installed on a computer in such a way that it can communicate with its practice management system software. Preferably this software is installed locally and will be generally referred to herein as "resident software". The resident software is preferably installed when the service provider accesses a portal web site via the internet using its internet service provider, as will be described in more detail below. The resident software is responsible for gathering claims and other data from the service provider's practice management system, creating and maintaining connections with the portal and payers, formatting claims data in acceptable ways to payers, transmitting the formatted claims to the payers and transmitting claims submission information to the portal. The resident software would also gather and aggregate data from Payers and display that data and claims submission information from the payers to the service provider and pull software updates from the portal.

At the portal, following completion of certain administrative formalities, the resident software may be downloaded to the local computer. The portal is responsible for providing profile information, storing payer configuration information for download to service providers, storing claim transaction information, and storing updates of the resident software. Profile information generally refers to the name of the service provider, its addresses, telephone numbers, email addresses, users, specialties of the service provider, bank name, bank address and routing number, credit card type and account number, employer identification number, and so forth.

Additionally, the service provider must register with payers that have web sites that provide for claim filing. Thus, the present system is for use in connection with (1) service providers that have practice management systems that generate billing files and (2) payers that permit on-line filing of claims but neither of these is part of the present invention. The present system does facilitates the filing of claims by the service provider by enabling it to format the billing files and to access the appropriate pages of the payers' web sites where those formatted files can be filed. The portal obtains the filing information from the payers' web sites, which information is constantly changing, and transfers that information to the resident software when the service provider is ready to file a batch of claims so that the service provider can successfully file claims directly with the payers via the internet.

The portal also helps the service provider keep track of the claims that have been submitted and the status of payment. The portal transmits data to a server that acts as a primary database. The primary database operates independently with a second, backup server acting as a backup database in case of failure of the first. Data in the first database is replicated to the backup database to minimize risk of loss.

The service provider, at intervals, will direct the resident software to file claims with the payers. The resident software will assemble the information needed to prepare billing data for each claim from the practice management system. These data are usually generated and identified by payer as they are created using the payer's unique five digit identification code. Some practice management software programs create a print image of the HCFA 1500 form; others simply create a data file for each claim.

The first component of the present system is the service provider's computers programmed with software that is in communication with the practice management software that may be installed on the same computer, or, alternatively, on a computer networked with that computer. The software on the service provider's computer that is part of the first component of the present invention will sometimes be referred to herein as local or resident software.

The resident software instructs the computer to copy the billing data generated by the practice management software and form a data stream. The location of the billing files is identified to it beforehand and its location incorporated into the local software instructions. The local software then compares the payer numbers on the billing data to the numbers on a pre-designated list of payers to determine if any are not present on the list. For example, some payers may not have web sites that permit online entry of claims. The claims to be filed with these payers would have to be filed via a different route such as by mailing a paper claim or through a clearinghouse. The software then instructs the computer to reject those billing data files that are intended for payers not on the list.

The local software will then access the second component of the present invention, namely, a web portal hosted by a server, via the healthcare service provider's usual internet service provider (ISP). This step is taken for two reasons. First, the local software may need to be upgraded in order to format the billing data in accordance with the current requirements of the payers. Second, the local software needs to know how to navigate to and through the payers' web sites to the pages where claims can be filed. The first portion of this information is downloaded to the local software from the web portal and becomes part of the permanent software until changed. The second part of the information to be obtained at the web portal, namely, the addresses of the payer's web sites at which online claim filing is to take place, is designed to expire within a relatively short period of time after the claims have been filed, as will be explained more fully below.

At the web portal component, the identity of the service provider is authenticated. Although this web site is preferably available via the internet, it is not a public site that can be found using the usual search engines. Alternatively, the web portal can be part of a private internet.

At this web portal, the version of the local software installed on the service provider's computer is compared with the most recent version stored on the server hosting the web portal and, if different, the most recent version is downloaded to the service provider's computer, replacing the older version stored there. Each payer may have changes, so there may be one software program that formats billing data for all payers in accordance with their individual formatting requirements or there may be a separate software formatting program for each payer, and consequently, a current version of that claim formatting software for each payer.

In addition to any upgrades needed to meet format requirements, a cookie is set in the local software that points to an address on the internet where the payer's web site permits electronic, online filing of claims. A cookie is a data pair set on the computer of a party when it accesses a web site. Cookies are customarily used to simplify the downloading of web pages the site visitor has visited before and to track the number of times the visitor has visited a web site and the visitor's navigation through a site. In the present invention the cookie includes the address of a page of the web site where claims can be filed on line and the number of the payer to which that web site corresponds. This information acts as a browser bookmark to direct the resident software to and through the payer's web site to the page where electronic copies of formatted claims can be filed.

The cookie is retrieved by the local software and applied to direct each claim in the billing data to the page of the payer's web site where that claim is to be filed. Upon reading the code number of the first payer on the billing data stream, the local software instructs the service provider's computer to log onto that payer's web site and navigate though the site to the web page that permits claim filing. The billing data stream is reformatted in accordance with the version of the formatting software installed on the local software, which then proceeds to reformat the billing data and file the claim. The claim is then filed by downloading the formatted data stream to the payer's web site or by simulating the keying of data into that payer's web site.

The payer's web site authenticates that the service provider is permitted to file claims with it and then begins to receive the electronic claims as transmitted. In the event a claim is rejected by the payer's web site, it will be returned to the service provider's practice management system for correction or special handling. Otherwise, the electronic claims that are not returned are accepted for processing. The payer's web site prepares a claims status report for the service provider for all claims previously filed and transmits that report as part of that session. A claims status report for all claims accepted for processing at the current session will be prepared and placed in a data file for transmission to the service provider the next time the service provider logs onto the payer's web site.

The web portal, in order to provide the software upgrade and cookie for the service provider, polls the web sites of the payers at intervals to determine if these web sites have announced any format changes. It also conducts a "dry run" for claim filing by accessing the payer's site, logging on, and proceeding through a sequence of pages to locate the page where claims are entered. This page is identified in the cookie.

The service provider connects to the portal to submit transaction information, to validate and update the client resident software with new versions, and to authenticate the portal so that it can retrieve provider profile and payer transmission information. This interface takes place upon installation, upon login, prior to submitting claims to payers, upon completion of claims submission to payers, and upon completion of data extraction routines.

The service provider connects directly with the payer's web site to submit claims data and receive error/response information as soon as it extracts claims data from the service provider's practice management system.

If the payer utilizes a non-Internet claims collection system (such as a bulletin board system), the service provider can access the web portal, which will redirect the connection to an analog "access server". This device will connect via standard analog connection to the payer to send claims.

There are a number of objects used in the resident software and the portal software. These objects are software objects as that term is customarily understood in connection with object-base programming. Each object has encapsulated data and methods. The following is a list of the primary objects on each along with a brief description of its function.

The first object on the resident software is the "execution" object that launches the application. This object calls all the supplemental objects. A number of the supplemental objects are for graphic user interface but others allow the user to execute aspects of the residential software. One of the supplemental objects is an "activity manager" object. This object tracks both the resident software activity and the portal activity. Each time the method of this software object is called, it posts a stream of data containing basic information (such as the activity type and method) in the form of a database line item insertion to the portal and as a text file each to the portal.

The resident software has a "log in manager" that verifies the presence of a live internet connection and a certificate verifying the service provider has registered, and then authenticates the user with a user name and password. Once authenticated, the software permits connection to the portal. The live internet connection is needed to download the resident software initially and download upgrades to that software thereafter.

Another object is a "browser connect" object that launches a browser window and loads a preselected web page. The browser functions an operating system.

Next, there is a "claims extraction manager" object that connects the resident software to the practice management system of the service provider. The claims extraction manager moves a copy of the billing file to the same computer where the resident software resides, reads it, validates it and parses the file. It sorts and formats the file by payer.

Another supplemental object on the resident software is the "download payer profile" object which downloads a "payer profile" object to the resident software so that the resident software can access the payer's website and file a claim. This object is a cookie, as described above.

There is an object for posting direct claims to and gathering responses from a payer. This object reads the payer profiles from the payer profile object to determine the type of connection system employed by the payer and calls the appropriate connection method. It then compresses the response files and pushes them to the portal. Then the response file is called.

An exit object terminates execution of the software, breaks connection to the portal and closes the client window. A related object breaks the connection to the portal by sending a disconnect message from the client and expiring the session.

The "download provider profile" object checks the version of the provider profile, downloads the entire object and, after checking to see if the provider profile is the most current version, applies the most current version.

Another supplemental object, the "upload software version" object, checks the version of the resident software and downloads and applies the most current version when appropriate. It achieves this result by comparing the file version on the resident software with the portal version via an HTTP (hypertext transfer protocol) post of the object version numbers and a return HTTP response from the portal with those objects that have been revised. The resident software then loads the files into the appropriate location.

Another object connects to the practice management system, moves a copy of the statement file to the local computer, reads and validates the file and formats when necessary.

A supplemental object posts claims to the payer and gathers the "adjudicated" responses. It first reads the payer and provider profiles, and then navigates to the claims submission page of the payer's web site. Individual claims are posted and responses accumulated by this object in a file format. The response files and transactional information are compressed and "pushed" to the portal. Finally, the response file viewer/printer is called by this object to display the adjudicated responses to the customer.

Related to this object is another object, a "payer connection management" object, that establishes a connection to the web site of the payer, authenticates the user and navigates to the claims submission page. A "transmission activity manager" object tracks the process of transmitting data such as claims by writing or recording a record in a file stored locally. This file is for recovery by the resident software.

These foregoing objects are the main objects on the resident software. The following objects are the main ones on the portal.

There is a gateway servlet object on the portal that handles all HTTP requests from users. This servlet object is essentially a traffic director when multiple users are attempting to log onto the portal. An "install user" object records the information entered by a user on the portal download page when the resident software is downloaded by a service provider.

A "user" object identifies registered users to the portal within a given service provider's account, offers registration to the users, verifies portal roles and returns the correct profile templates and data for portal users. The user object is verified for portal eligibility and then populated with the correct profile information for the user within an account for the duration of the session.

A "user password finder" object retrieves user-related information such as a user name, account number, and user password, and stores them into the session context if the user name and account numbers match the same fields in the database. A related object, the "user question validation" object retrieves the user password question and password answer from the session context and compares the answer from the user against the same password answer in the session context. If the passwords match, the password is reset. Otherwise password mismatch message is provided to the user.

There is an "alert" object that reads and writes alerts to and from the database, and an "administrative payer" object that allows administrative personnel to perform administrative functions through the portal, namely, add, update, and delete payer-specific information.

An "account" object identifies registered accounts with the portal and offers registration options for the portal. The account object is verified for portal eligibility and then populated with the correct profile information for the duration of the session for that account.

There is an object that defines the process for identifying which accounts are registered with specific payers, another object responsible for managing the data for the account practice management system, and one for identifying the location of the accounts the practice management system files and modifying the location of those files.

An "activity manager" object captures pre-defined activities performed by a user and stores a record in the database when an action is performed. This manager object provides a method for tracking which action has been performed in the event an error occurs.

A "session manager" object, which is the object called by the "servlet gateway" object, performs user validation. In particular, it passes the user name and password to the "user" object that will access the database for the user validation. It will then store the user session information in the session context.

A "client version verification manager" object manages the updates of the present system's resident software. It determines if the account is operating and whether it has the most recent version of the software, and then updates those files of that account that require it. To determine which files on the resident software that need to be updated, a version number is maintained on each file in the portal database. This number is compared to the number on the corresponding files on the service provider's resident software. The updates are downloaded.

The "client update manager" object submits a request for a specific version of the object to the portal. The portal responds with the requested version of the object. A "response manager" object retrieves and stores for the portal the various response files that have been generated and aggregated on the resident software.

The "portal bridge" object manages connections between the resident software and the access server. It establishes a secure socket layer connection to the resident software, and a transmission control protocol/internet protocol (TCP/IP) connection to a modem connected to an access server. The resident software can then initiate an analog dial out to a payer bulletin board system.

There are several other administrative type objects such as an object that enables a user with an account to retrieve and view a claim submission history on-line, one that allows a user to retrieve and view a payment history on line, one to gather and store transaction information supplied by the service provider, one to modify contact information, one for credit card information and one for bank information for a given account. The credit card and bank information is required in order for the service provider to pay for the service provided by the present system.

In use, a user from the service provider's office will start up the local computer and access the internet through its usual internet service provider. Once logged onto the internet, the user will go to the public part of the portal site.

The user that enters the portal web site from the internet will have access to limited functionality within the portal. The profile administration and help functions will be available but the user will not be able to process claims and electronic patient statements from the public portion.

To access the portal, the user must have a desktop computer connected to the internet, have navigated to the portal web site, and have a suitable web browser installed. Once at the web portal site and authenticated, the user will be given access to portal resources at the portal home page.

To be authenticated, the user must be a registered user of the portal, be connected to the internet and have the resident software installed on the user's desk top computer. The user is then able to launch the local application, which will request access to the private portion of the portal. The portal will pass the authentication message back to the resident software. The portal and resident software will then be in communication, and the user will have access to all portal functions corresponding to the user's role and the functions associated with that role. For example, if the user is not an administrator, it will not have access to administrative functions.

At this point, the most recent version of the resident software is downloaded from the portal to the service provider's computer. If the user does not have any version, it can download the software from the public portion of the portal site. This software may also be installed on the service provider's computer using a compact disk. If the software is being installed for the first time and not simply being upgraded with the latest version, the user will need to supply certain profile information: salutation, first name, last name, e-mail address, state where practice is located, zip code, and practice specialty. The portal will confirm with the user the location where the software is to reside and then begin the download. The user will then be given instructions as to how to launch the application for installation and what information will be collected during installation.

During installation, the user's internet connection is checked and then various information is requested. This information includes customer information, account and billing information, information about the user's practice management system, billing file information, names of payers where the user has an "electronic relationship" (is registered with that web site as a party able to file claims there), and user names and passwords for payer sites. The user is given the opportunity to confirm all information and to select certain options such as the option to have printed copies of claims mailed to it. Next, the user is given instructions as to how to log in and told what information will be requested upon logging in.

This registration information is checked to see that it is unique and not a duplicate of information previously entered. If the information is indeed unique, the registration is complete.

The portal checks the version of resident software when that version identifier is passed from the resident software to the portal. The identifier is compared by the portal to the current version and, if the resident software version is not the latest, the latest version is downloaded.

At the same time, the payer transmission profile and decision matrix is downloaded and the service provider's user is notified of the download.

To process claims, the claim information is extracted from the service provider's practice management system. The resident software establishes a connection to the practice management system, locates the billing file, loads it, and extracts the claims data from it. The claims data must then be formatted, sorted and prepared for submission to a payer. For present purposes, a "payer" is a payer with a web-based presence that accepts filing of claims at its web site, a payer that accepts claims when a direct connection is made, and a clearinghouse that will print and mail paper-based claims. In order to format, sort and prepare the claims data, they must be parsed to determine their current format and to allow them to be sorted by payer, then the data are sorted by payer and formatted according to each payer's specifications. Each set of claims (corresponding to a different payer) is placed into a separate file, the claims counted and the file closed.

The claims are then filed with each payer, one payer at a time. The payers confirm to the local software that each claim was successfully filed. If any failed to transmit, that information is provided to the resident software and displayed for the user. While logged onto payer's web sites or connected directly with payers, the user may retrieve responses to claims previously filed.

The user may obtain a transaction activity summary describing the claims processed, including statistics, the number of claims submitted per payer and data and time claim was processed. The user will have the capability to search for a particular transaction, as well. The transaction summary is posted to the portal which displays it to the user in a form that is readily grasped and may be manipulated to display the transaction information in useful ways. This is an important feature of the present invention because it enables the user to obtain information about is claims processing that it currently does not have and which can be used to manage the service provider's practice better.

It will be apparent to those skilled in processing insurance claims that many changes and substitutions can be made to the foregoing preferred embodiments without departing from the spirit and scope of the present invention, which is defined by the appended claims.

What is claimed is:

1. A method for enabling a practice management system of a service provider to file an insurance claim electronically via a payer's web site, said insurance claim being based on billing data stored on said practice management system, said method comprising the steps of:
    electronically locating billing data stored on a practice management system of a service provider;
    electronically eliminating a portion of said billing data intended for payers that do not permit online filing of claims;
    downloading from a payer's web site to a web portal format instructions for formatting billing data for online filing of insurance claims at said payer's web site, said portal operated by a third party who is not a prayer nor said service provider;
    determining by said web portal an address at said payer's webs site for filing insurance claims;
    conveying from said web portal said format instructions and said address to said practice management system of said service provider;
    said practice management system electronically accessing said payer's web site;
    said practice management system electronically navigating to said payer's web site to said address where said insurance claims can be filed;
    then electronically formatting said billing data in accordance with said format instructions to generate insurance claims; and
    then uploading said insurance claims to said payer's web site.

2. The method as recited in claim 1, wherein said conveying step further comprises the step of setting a cookie in said practice management system by said web portal, said cookie containing said address of said payer's web site.

3. The method as recited in claim 1, wherein said conveying step further comprises the steps of:
    comparing format instructions on said practice management system with instructions downloaded from said payer's web site to determine if said format instructions on said practice management software are current; and
    conveying said downloaded format instructions if said format instructions on said practice management software are not current.

4. The method as recited in claim 1, further comprising the step of polling by said web portal said payer's web site for changes in format instructions.

5. The method as recited in claim 1, wherein said determining step further comprises the steps of:
    logging onto said payer's web site; and
    navigating said payer's web site to locate said address for filing billing files.

6. A system for filing an insurance claim at a web site operated by a payer, said web site permitting electronic filing by a service provider of billing data formatted as an insurance claim said system comprising:
    a web portal, operated by a third party who is not a payer nor said service provider, programmed to obtain from each web site of plural web sites that permit electronic filing of insurance claims, insurance claim formatting instructions and a web page location for filing said formatted billing data, wherein each web site is operated by a different payer; and
    a computer operated by a service provider having access to stored billing data and programmed to log on to said web portal to receive said format instructions and said web page location from the portal, said computer programmed to retrieve and format said billing data in accordance with said format instructions and to file said formatted data files as insurance claims at said web page location.

7. The system as recited in claim 6, wherein said web portal further comprises means for setting a cookie containing said web page address in said computer.

8. The system as recited in claim 6, wherein said web portal further comprises means for uploading changes to said format instructions to said computer when said computer accesses said portal.

9. The system as recited in claim 6, wherein said web portal further comprises means for polling web sites of said payers for changes in said format requirements.

10. A system for filing insurance claims at plural web sites, each web site operated by a different payer, said plural web sites permitting electronic filing of insurance claims based on billing data said system comprising:
    means for collecting billing data located on a practice management computer system of a service provider;
    a web portal for obtaining from each web site format instructions and a web page location for filing an insurance claim, said portal operated by a third party different from said payers and said service provider;
    means for download from said web portal to said practice management computer system said format instructions and said web page location;
    means for logging said practice management computer system onto said each web site in sequence and navigating to each web page location obtained by said web portal;
    means located on the practice management computer system for automatically formatting said billing data in accordance with said format instructions obtained by said web portal to create insurance claims; and
    means for uploading said insurance claims to said each web page location from said automatic formatting means.

11. The system as recited in claim 10, wherein said web portal sets a cookie containing said web page location in said logging means.

12. The system as recited in claim 10, wherein said web portal polls said web site operated by a payer to obtain changes in said format instructions and conveys said changes to said formatting means.

* * * * *

UNITED STATES PATENT AND TRADEMARK OFFICE
CERTIFICATE OF CORRECTION

| | | |
|---|---|---|
| PATENT NO. | : 7,668,738 B2 | Page 1 of 1 |
| APPLICATION NO. | : 09/794741 | |
| DATED | : February 23, 2010 | |
| INVENTOR(S) | : Wiggins | |

It is certified that error appears in the above-identified patent and that said Letters Patent is hereby corrected as shown below:

Claim 1 (column 11, line 25) should read as follows:

operated by a third party who is not a payer nor said Claim 1 (column 11, line 28) should read as follows:

web site for filing insurance claims;

Signed and Sealed this

Twenty-seventh Day of July, 2010

David J. Kappos
*Director of the United States Patent and Trademark Office*